| United States Patent [19] | [11] | 4,160,784 |
|---|---|---|
| Sugasawa et al. | [45] | Jul. 10, 1979 |

[54] PROCESS FOR THE PRODUCTION OF o-AMINOPHENYL KETONE DERIVATIVES

[75] Inventors: Tsutomu Sugasawa, Kobe; Tatsuo Toyoda, Osaka; Makoto Adachi, Izumi; Kazuyuki Sasakura, Oumihachiman, all of Japan

[73] Assignee: Shionogi & Co., Ltd., Osaka, Japan

[21] Appl. No.: 770,037

[22] Filed: Feb. 18, 1977

[30] Foreign Application Priority Data

Feb. 18, 1976 [JP]  Japan ................................. 51-16677

[51] Int. Cl.$^2$ ............................................. C07C 85/18
[52] U.S. Cl. ......................... 260/570 AB; 260/551 B; 260/566 R; 260/570.5 P; 260/575; 260/577; 260/578
[58] Field of Search ............ 260/570 AB, 578, 566 R, 260/575, 577

[56] References Cited

PUBLICATIONS

Olah, "Friedel–Crafts and Related Reactions", vol. III, Part I, pp. 394–408 (1964).
Olah (II), "Friedel–Crafts and Related Reactions", vol. I, pp. 517–518 (1963).
Sidgwicke, "The Organic Chemistry of Nitrogen", p. 446 (1966), 3rd Ed.

*Primary Examiner*—Robert V. Hines
*Attorney, Agent, or Firm*—Wenderoth, Lind & Ponack

[57] ABSTRACT o-Aminophenyl ketone derivatives are regio-specifically prepared by reacting an aniline unsubstituted in at least one ortho position with a nitrile in the presence of boron trihalogenide to introduce a substituted iminomethyl into the ortho position of said aniline and hydrolyzing the resulting iminomethyl compound.

7 Claims, No Drawings

PROCESS FOR THE PRODUCTION OF o-AMINOPHENYL KETONE DERIVATIVES

The present invention relates to a chemical process in the production of o-aminophenyl ketone derivatives by introducing regiospecifically a substituted iminomethyl group into one of the ortho positions of anilines and hydrolyzing the iminomethyl group into the corresponding acyl group. Namely, this invention is concerned with a process for preparing anilines having an acyl group in an ortho position.

For introducing an acyl group into an ortho position of anilines, for example, the Friedel-Crafts reaction has heretofore been adopted, requiring severe condtions such as heating at 200° C. and then with conc. hydrochloric acid for more than 20 hours to give p-acylanilines as main products. Therefore, the scope of the starting anilines to which said method can be applied is limited to certain anilines stable to heating and strong acid, and the yield of the product is insufficient. The other several methods also have the same or different serious defects such as requiring several steps. Because of these and other defects, there can be found no process for preparing economically and conveniently o-aminophenyl ketone derivatives.

Noting that various o-aminophenyl ketone derivatives are utilized as starting materials in chemical industries and important synthetic intermediates for medicinals, the present inventors have investigated development of a new synthetic economical process in a broad scope of application and established the process of the present invention which meets these requirements.

The process of the present invention comprises (1) reacting an aniline unsubstituted in at least one ortho position with a nitrile in the presence of boron trihalogenide to introduce a substituted iminomethyl into the ortho position of said aniline and (2) hydrolyzing the resulting iminomethyl compound. One of advantageous points in the present invention consists in a broad scope of application. The reaction model in which aniline is used as a starting compound is illustrated for ready understanding in the following scheme:

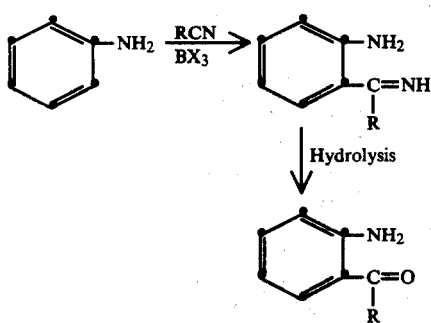

(wherein R is alkyl, aralkyl, or aryl; and X is halogen.)

The starting compound is an aniline unsubstituted in at least one ortho position, which may have one or more substituents as long as they are inactive during the course of the present process. Said aniline involves aniline, N-monosubstituted anilines, anilines substituted on the benzene ring, and N-monosubstituted anilines substituted on the benzene ring. Examples of the substituent on the benzene ring of anilines are alkyl, alkoxy, halogen, nitro, aryl, aryloxy, aralkyl, aralkoxy, alkylthio, arylthio, alkylsulfinyl, arylsulfinyl, alkylsulfonyl, arylsulfonyl, and the like. The process of the invention is smoothly carried out by using an aniline preferably having only one or two substituents selected from alkyl, alkoxy, and halogen on the benzene ring of the aniline.

Examples of the N-monosubstituent of anilines are alkyl, aralkyl, and aryl, and these hydrocarbon groups may be substituted by one or more substituents which are inactive during the course of the present process and which involve illustratively those shown above for substituents on the benzene ring.

The definition of the above substituents both on the benzene ring and on the amino can be complemented by the following illustration. The alkyl involves methyl, ethyl, propyl, butyl, pentyl, and hexyl. The alkoxy involves methoxy, ethoxy, propoxy, butoxy, pentyloxy, and hexyloxy. The halogen involves chlorine, bromine, fluorine, and iodine. The aryl involves phenyl, tolyl, xylyl, naphthyl, pyridyl, thienyl, and furyl. The aryloxy involves phenoxy, naphthoxy, pyridyloxy, furyloxy, and tolyloxy. The aralkoxy involves benzyloxy, phenethyloxy, phenylpropoxy. The aralkyl involves benzyl, phenethyl, phenylpropyl, phenylbutyl, naphthylethyl, and pyridylmethyl. The alkylthio involves methylthio, ethylthio, propylthio, butylthio, pentylthio, hexylthio, and heptylthio. The arylthio involves phenylthio, tolylthio, naphthylthio, and pyridylthio. The alkylsulfinyl involves methylsulfinyl, ethylsulfinyl, propylsulfinyl, butylsulfinyl, pentylsulfinyl, and hexylsulfinyl. The arylsulfinyl involves phenylsulfinyl, tolylsulfinyl, naphthylsulfinyl, and pyridylsulfinyl. The alkylsulfonyl involves methylsulfonyl, ethylsulfonyl, propylsulfonyl, butylsulfonyl, and pentylsulfonyl. The arylsulfonyl involves phenylsulfonyl, tolylsulfonyl, naphthylsulfonyl, and pyridylsulfonyl.

The boron trihalogenide used in the present process involves illustratively boron trichloride and boron tribromide.

Another starting material, i.e. the nitrile, involves alkylnitrile, arylnitrile, and aralkylnitrile. The hydrocarbon group of nitriles may be substituted by one or more substituents selected from alkyl, alkoxy, halogen, and nitro. Typical examples of the nitrile are acetonitrile, propionitrile, butyronitrile, benzonitrile, phenylacetonitrile, furancarbonitrile, and those substituted by alkyl, alkoxy, and halogen, preferably monochloro, dichloro, trichloro, nitro, and methoxy. Preferred examples of the nitrile are benzonitrile, acetonitrile, phenylacetonitrile, 2-chloroacetonitrile, propionitrile, 4-chlorobutyronitrile, o-chlorobenzonitrile, m-nitrobenzonitrile, and trichloroacetonitrile.

The process of the present invention consists in two steps; (1) a step in reacting an aniline with a nitrile in the presence of boron trihalogenide to produce an anilinodihaloborane [The formation of anilinodihaloborane has been affirmed by K. Niedenzu and J. W. Dawson, J. Am. Chem. Soc., 81, 5553, (1959); and W. Gerrard and E. F. Mooney, J. Chem. Soc., 4028 (1960).] and then introduce regiospecifically a substituted iminomethyl into an ortho position of said aniline and (2) a step in hydrolyzing the resulting iminomethyl compound to produce the corresponding ketone compound. In fact, however, the process can be performed either stepwise by isolating the intermediary iminomethyl compound or continuously without isolating the iminomethyl compound.

At first the reaction of an aniline with a nitrile in the presence of a boron trihalogenide is below described in detail. This step can be effected by treating an aniline, boron trihalogenide and a nitrile in the presence or absence of a suitable inert solvent (e.g. methylene chloride, dichloroethane, benzene, toluene, xylene) in the range of from room temperature to the boiling point of the solvent used. A preferred upper limit of the temperature range is about 200° C. A preferred range of time for the reaction is from about 1 to about 25 hours. Although the reaction proceeds smoothly in general, the yield of the product can be raised by adding a suitable Lewis acid (e.g. aluminum chloride, titanium tetrachloride, stannic chloride). Furthermore, the reaction may be carried out under nitrogen atmosphere for inhibiting occurrence of side reactions. The yield of the product can be occasionally raised as a variant of this step by reacting previously an aniline with boron trihalogenide to give the anilinodihaloborane and then reacting the isolated anilinodihaloborane, with a nitrile. Preferred ranges for proportions of a nitrile, boron trihalogenide and Lewis acid, to 1 mol of the aniline, are about 1—about 3, about 1–about 1.5, and about 1–about 1.5 mol equivalent, respectively.

Secondly, thus-produced iminomethyl compound can be easily hydrolyzed with an acid or alkali to give the corresponding ketone compound. The hydrolysis is effected by using an acid (e.g. hydrochloric acid, sulfuric acid, acetic acid) or an alkali (e.g. sodium hydroxide, potassium ethoxide) at room temperature or under heating below 100° C., if necessary, in a suitable solvent (e.g. water, ethanol, methylene chloride, dioxane, dimethylformamide, a mixture thereof). A preferred range of time for hydrolysis is below about 1 hour.

If desired, the iminomethyl compound can be isolated by making the reaction mixture in the first step alkaline to give an iminodialkoxyborane and treating the isolated iminodialkoxyborane with a weak acid. (e.g. acetic acid).

The o-aminophenyl ketone derivatives are useful in a broad scope as starting materials in chemical industries or important intermediates in the production of medicinals.

Presently-preferred and practical embodiments of the present invention are illustratively shown in the following examples.

EXAMPLE 1

To a solution of aniline (466 mg) in dichloroethane (5 ml), a solution of boron trichloride (640 mg) in dichloroethane (2.1 ml), benzonitrile (1 ml) and aluminum chloride (734 mg) are added under ice cooling, and the mixture is refluxed for 6 hours. After cooling, the mixture is mixed with 2 N hydrochloric acid (10 ml) and heated at 70° to 80° C. for 20 minutes to hydrolyze 2-(phenyliminomethyl) aniline and the extracted with methylene chloride. The methylene chloride layer is washed with dilute hydrochloric acid, evaporated to remove the solvent, and the residuary benzonitrile is evaporated under reduced pressure. The residue is recrystallized from methylene chloride/n-hexane to give 2-aminobenzophenone (619 mg) as crystals melting at 107° to 108° C. The yield is 63%.

EXAMPLES 2–4

Using the starting compounds (II) and (III), each reaction is carried out as in Example 1, whereby the corresponding products (I) are obtained as shown in Table 1.

Table 1.

| | | Reaction Conditions | | | I | |
|---|---|---|---|---|---|---|
| Example No. | R | Solvent | Lewis acid | Reflux time (hr) | m.p. (°C.) | Yield (%) |
| 2 | Me | (CH₂Cl)₂ | AlCl₃ | 5 | 79* | 60 |
| 3 | Bz | (CH₂Cl)₂ | AlCl₃ | 5 | 102–103 | 76 |
| 4 | ClCH₂ | (CH₂Cl)₂ | AlCl₃ | 3 | 112–113 | 52 |

Note:
*N-Acetate.
The abbreviations in the table mean as follows: Me (Methyl); Bz (Benzyl).

EXAMPLE 5

To a solution of p-chloroaniline (640 mg) in tetrachloroethane (5 ml), a solution of boron trichloride (640 mg) in tetrachloroethane (2.5 ml), benzonitrile (1 ml) and aluminum chloride (734 mg) are added under ice cooling, and the resultant mixture is refluxed for 6 hours. After cooling, the reaction mixture is mixed with 2 N hydrochloric acid (10 ml), heated at 70° to 80° C. for 20 minutes, and shaken with methylene chloride. The methylene chloride layer is evaporated to give a residue, to which 95% ethanol (5 ml) and 2 N sodium hydroxide (10 ml) are added. The mixture is refluxed for 1 hour to hydrolyze benzonitrile and shaken with methylene chloride. The methylene chloride layer is evaporated, and the residue is dissolved in benzene and chromatographed on a column of alumina, which is eluted with benzene. The benzene eluate affords 2-amino-5-chlorobenzophenone (486 mg), which is recrystallized from ether to give crystals melting at 99° C.

EXAMPLE 6

(1) The reaction is repeated as in Example 5, except that the reaction mixture is mixed with 2 N sodium hydroxide (50 ml) and extracted with methylene chloride. The methylene chloride layer is dried over potassium carbonate and chromatographed on a column of alumina, which is eluted with methylene chloride/methanol (10/1). The eluate affords 4-chloro-2-[phenyl-(N-dimethoxyborylimino)methyl]aniline (237 mg), which is recrystallized from methanol to give crystals melting at 150° to 152° C. (decomp.).

IR (CHCl₃), 3638, 3405, 3350, 1623, 1545 cm⁻¹.

(2) The above product is mixed with benzene (2 ml) and 0.1 N acetic acid (2 ml), and the resultant mixture is stirred at room temperature for 20 minutes. The reaction mixture is made alkaline with sodium hydroxide. The benzene layer is evaporated to give a residue, which is recrystallized from petroleum ether to give 4-chloro-2-(phenyliminomethyl)aniline as crystals melting at 74° C. [Netherlands Pat. No. 6,507,637]. The product is hydrolyzed to give 2-amino-5-chlorobenzophenone.

EXAMPLE 7

To a solution of m-anisidine (616 mg) in dry benzene (6 ml), a solution of boron trichloride (59 mg) in dry benzene (2 ml), 2-chloroacetonitrile (453 mg) and aluminum chloride (734 mg) are added, and the resultant mixture is stirred at room temperature for 15 hours. The reaction mixture is mixed with 2 N hydrochloric acid (20 ml), heated on a boiling water bath for about 30 minutes, diluted with water, and shaken with methylene chloride. The methylene chloride layer is evaporated to give a residue, which is chromatographed on a column of alumina to give 2-amino-4-methoxy-ω-chloroacetophenone (499 mg) as crystals melting at 103° to 104° C. and 2-amino-6-methoxy-ω-chloroacetophenone (25 mg) as crystals melting at 134° to 135° C.

EXAMPLES 8–23

Using the starting compounds (II) and (III), each reaction is carried out as in Example 1, whereby the corresponding products (I) are obtained as shown in Table 2.

EXAMPLE 24

To a solution of N-methylaniline (277 mg) in benzene (5 ml), a solution of boron trichloride (303 mg) in benzene (2 ml) is added, and the resultant mixture is refluxed for 4 hours under nitrogen atmosphere. The reaction mixture is evaporated to remove the solvent. To the residue is added benzonitrile (1 ml), and the mixture is heated on a water bath at 100° C. for 4 hours. The reaction mixture is treated as in Example 5 to give 2-methylaminobenzophenone (477 mg) as crystals melting at 66° to 68° C. The yield is 87%.

EXAMPLE 25–27

Using the starting compounds (II) and (III), the reactions are carried out as in Example 24, whereby the corresponding products (I) are obtained as in Table 3.

Table 2.

| | II | | III | Reaction Conditions | | | I | |
|---|---|---|---|---|---|---|---|---|
| Example No. | $R^1$ | $R^2$ | R | Solvent | Lewis acid | Reflux Time (hr) | mp (°C.) or IR (cm$^{-1}$) | Yield (%) |
| 8 | Me | H | o-Cl—Ph | TE | — | 6 | 68–70 | 53 |
| 9 | Me | H | m-NO$_2$—Ph | TE | — | 3 | 117–119 | 56 |
| 10 | Me | H | Et | BN | AlCl$_3$ | 20 | 39–40 | 79 |
| 11 | Me | H | Bu | BN | AlCl$_3$ | 20 | 122–123 | 67 |
| 12 | Me | H | Bz | BN | AlCl$_3$ | 20 | 65–66 | 64 |
| 13 | Me | p-Cl | Ph | TE | AlCl$_3$ | 5 | 94–95 | 62 |
| 14 | DA | p-Cl | Ph | TE | AlCl$_3$ | 3 | 192–193* | 79 |
| 15 | Me | m-F | Cl(CH$_2$)$_3$ | TE | AlCl$_3$ | 5 | 1698,1660* (CHCl$_3$) | 49 |
| 16 | Me | m-Cl | Cl(CH$_2$)$_3$ | TE | AlCl$_3$ | 5 | 3330,1630 (CHCl$_3$) | 61 |
| 17 | H | m-F | Cl(CH$_2$)$_3$ | BN | AlCl$_3$ | 5 | 66–67*(1) 73–74*(2) | 57 4 |
| 18 | H | m-Cl | Cl(CH$_2$)$_3$ | BN | AlCl$_3$ | 8 | 61–62* | 67 |
| 19 | H | p-Met | ClCH$_2$ | BN | TiCl$_4$ | 3 | 103–104 | 40 |
| 20 | H | o-Cl | ClCH$_2$ | BN | AlCl$_3$ | 6 | 61–62 | 63 |
| 21 | H | p-Cl | ClCH$_2$ | BN | AlCl$_3$ | 6 | 140–141 | 66 |
| 22 | H | m-Cl | ClCH$_2$ | BN | AlCl$_3$ | 6 | 60–61(3) 134–135(4) | 14 52 |
| 23 | H | m-Met | ClCH$_2$ | BN | AlCl$_3$ | 15** | 134–135(5) 103–104(6) | 3 50 |

Note:
*N-Acetate;
**The reaction is carried out at room temperature.
The abbreviations in the table mean as follows:
Me (Methyl); Met (Methoxy); DA (Diethylaminoethyl); Ph (Phenyl); Et (Ethyl); Bu (Butyl); Bz (Benzyl); TE (Tetrachloroethane); BN (Benzene).
(1)2-Amino-4-fluoro-ω-chlorobutyrophenone
(2)2-Amino-6-fluoro-ω-chlorobutyrophenone
(3)2-Amino-4-chloro-ω-chloroacetophenone
(4)2-Amino-6-chloro-ω-chloroacetophenone
(5)2-Amino-4-methoxy-ω-chloroacetophenone
(6)2-Amino-6-methoxy-ω-chloroacetophenone Table 3.

$$R^2 \underset{(II)}{\overset{\text{NHCH}_3}{\bigcirc}} \xrightarrow{\text{RCN (III)}} R^2 \underset{(I)}{\overset{\text{NHCH}_3}{\underset{\underset{R}{|}}{\overset{|}{\bigcirc}-\text{C}=\text{O}}}}$$

| | (II) | (III) | (I) |
|---|---|---|---|
| Example No. | $R^2$ | R | mp (°C.) or IR (cm$^{-1}$) | Yield (%) |
| 25 | H | CCl$_3$ | 3370, 1650 (CHCl$_3$) | 76 |
| 26 | p-Cl | Ph | 94–95 | 69 |
| 27 | p-Cl | o-Cl—Ph | 88–90 | 61 |

Note:
The abbreviation means as follows:
Ph (Phenyl)

EXAMPLE 28

(1) To a solution of p-chloro-N-methylaniline (708 mg) in dichloroethane (7 ml), a solution of boron trichloride (640 mg) in dichloroethane (2.5 ml) is added under ice cooling. To the mixture are added benzonitrile (1.5 ml) and aluminum chloride (734 mg), and the resultant mixture is refluxed for 5 hours under nitrogen atmosphere. After cooling, the reaction mixture is treated as in Example 6 (1) to give 4-chloro-2-[phenyl-(N-diethoxyborylimino)methyl]-N-methylaniline (838 mg), which is recrystallized from methylene chloride/ethanol to give crystals melting at 153° to 156° C. while changing orange above 140° C. The yield is 49%.

IR (CHCl$_3$); 3628, 1618, 1590, 1523, 1472 cm$^{-1}$.

(2) The above product is treated as in Example 6 (2) to give 4-chloro-2-(phenyliminomethyl)-N-methylaniline (33 mg), which is recrystallized from methanol to give crystals melting at 96° to 97° C. The yield is 93%.

(3) The above product is hydrolyzed to give 5-chloro-2-methylaminobenzophenone.

EXAMPLE 29

The reaction is repeated as in Example 28 (1) except that o-chlorobenzonitrile is used in lieu of benzonitrile, whereby 4-chloro-2-[o-chlorophenyl-(N-diethoxyborylimino)methyl]-N-methylaniline (973 mg) is obtained as crystals melting at 156° to 165° C. (decomp.). The yield is 51%.

IR (CHCl$_3$); 3623, 3345, 1617, 1523, 1478 cm$^{-1}$.

(2) The above product (500 mg) is treated as in Example 6 (2) to give 4-chloro-2-(o-chlorophenyliminomethyl)-N-methylaniline (368 mg), which is recrystallized from isopropanol to give crystals melting at 63° to 64° C.

IR (CHCl$_3$); 3285, 3215, 1608, 1516 cm$^{-1}$.

What is claimed is:

1. Process for the production of o-aminophenyl ketone derivatives which comprises reacting an aniline unsubstituted in at least one ortho position with a nitrile in the presence of boron trihalogenide to introduce a substituted iminomethyl into the ortho position of said aniline and hydrolyzing the resulting iminomethyl compound.
2. Process according to claim 1, wherein the reaction is effected in the presence of a Lewis acid.
3. Process according to claim 1, wherein the boron trihalogenide is boron trichloride.
4. Process according to claim 1, wherein the reaction is effected in an inert solvent.
5. Process according to claim 2, wherein the Lewis acid is aluminum chloride.
6. Process according to claim 1, wherein the reaction of the aniline with the nitrile is carried out at a temperature from room temperature to 200° C.
7. Process according to claim 1, wherein the aniline has one or two substituents selected from the group consisting of alkyl of 1–6 carbon atoms, alkoxy of 1–6 carbon atoms and halogen on the benzene ring of the aniline.

* * * * *